US009378409B2

(12) United States Patent
Tsou et al.

(10) Patent No.: US 9,378,409 B2
(45) Date of Patent: Jun. 28, 2016

(54) EYE SEARCHING METHOD AND EYE STATE DETECTION APPARATUS AND EYE SEARCHING APPARATUS USING THE SAME

(71) Applicant: UTECHZONE CO., LTD., New Taipei (TW)

(72) Inventors: Chia-Chun Tsou, New Taipei (TW); Po-Tsung Lin, New Taipei (TW); Chih-Heng Fang, New Taipei (TW)

(73) Assignee: UTECHZONE CO., LTD., New Taipei (TW)

( * ) Notice: Subject to any disclaimer, the term of this patent is extended or adjusted under 35 U.S.C. 154(b) by 286 days.

(21) Appl. No.: 14/023,938

(22) Filed: Sep. 11, 2013

(65) Prior Publication Data
US 2014/0078284 A1   Mar. 20, 2014

(30) Foreign Application Priority Data

Sep. 14, 2012   (TW) .............................. 101133736 A

(51) Int. Cl.
*G06K 9/00* (2006.01)
*A61B 3/113* (2006.01)

(52) U.S. Cl.
CPC ............ *G06K 9/00248* (2013.01); *A61B 3/113* (2013.01); *G06K 9/00597* (2013.01)

(58) Field of Classification Search
CPC ................................................. G06K 9/00248
USPC ........................................................... 348/78
See application file for complete search history.

(56) References Cited

U.S. PATENT DOCUMENTS

| 5,573,006 | A | * | 11/1996 | Shimotani | ............ A61B 5/1103 340/575 |
| 6,304,187 | B1 | | 10/2001 | Pirim | |
| 6,549,644 | B1 | * | 4/2003 | Yamamoto | ......... G06K 9/00268 382/117 |
| 8,094,883 | B2 | | 1/2012 | Nagai et al. | |
| 8,184,008 | B2 | | 5/2012 | Uozumi et al. | |
| 8,224,035 | B2 | | 7/2012 | Adachi et al. | |
| 2008/0137959 | A1 | * | 6/2008 | Adachi et al. | .................. 382/190 |
| 2010/0220925 | A1 | * | 9/2010 | Ikeda | .................. G06K 9/00248 382/165 |
| 2010/0253806 | A1 | * | 10/2010 | Guan | .................. G06K 9/00281 348/231.3 |

FOREIGN PATENT DOCUMENTS

| CN | 101196993 B | 6/2012 |
| TW | 436436 B | 5/2001 |
| TW | I349214 | 6/2011 |
| TW | 201140511 A | 11/2011 |
| TW | M416161 U | 11/2011 |

* cited by examiner

*Primary Examiner* — Jamie Atala
*Assistant Examiner* — Kathleen Nguyen
(74) *Attorney, Agent, or Firm* — Muncy, Geissler, Olds & Lowe, P.C.

(57) ABSTRACT

The present invention relates to an eye searching method and an eye state detection apparatus and an eye searching apparatus using the same. The method comprises the steps of: defining each center point of two nostrils from a face image; computing a distance D between the two center points of the two nostrils and a midpoint between the two center points of the two nostrils; determining a reference point that has a horizontal distance k1×D and a vertical distance k2×D spaced apart from the midpoint, wherein k1=1.6~1.8, k2=1.6~1.8; and defining a rectangle around the reference point as its center, wherein the rectangle has a width and a length greater than the width, and the rectangle surrounds the eye of the face image. Accordingly, the present invention can quickly and accurately find out a certain part of the eye from the face image.

9 Claims, 3 Drawing Sheets

EYE SEARCHING METHOD AND EYE STATE DETECTION APPARATUS AND EYE SEARCHING APPARATUS USING THE SAME

BACKGROUND OF INVENTION

1. Field of Invention

The invention relates to an image processing technology, and more especially to a technology that can quickly and accurately find out an eye from a face image.

2. Related Prior Art

Technology related to eye state identification, such as detecting a driver's eye state to identify whether he/she is dozing off while driving, or detecting eye movement of a person suffering from Amyotrophic lateral sclerosis (ALS) for control purpose, has been widely known. Also, there are lots of patent applications, for example, Taiwan Patent No. 436436, I349214, M416161, TW 201140511, U.S. Pat. No. 8,094,883, U.S. Pat. No. 8,184,008, CN101196993 and so on, which describe an image processing method for eye state identification. The aforementioned technology comprises several steps, including capturing a user's face by a camera device to obtain images of the user's face, processing these images by an eye-identification device, and then determining the eye state of the user based on the processed results. The step of processing each of the images by the eye-identification device mentioned above further comprises the following sub-steps in sequence: finding out a face area, obtaining an eye area according to the face area that is found, attaining an specific area of the eye based on the eye area (such as upper eyelid, lower eyelid, or pupil), and determining the eye state of the user (i.e. whether the eye is opened or closed) according to variation of the specific area. However, how to find out the eye area on the face image quickly and precisely is one of the significant issues.

A conventional eye detection apparatus disclosed in China Patent No. 101196993 includes means for finding out positions of nostrils from a face image, means for establishing an eye searching area based on the positions of the nostrils, and means for attaining upper and lower eyelids from the eye searching area. It is understood that the nostrils on the face image is black, which therefore can be easily and precisely identified. Accordingly, in comparison with the traditional way to find out the eye directly from the face image, the eye detection apparatus can find out the eye more quickly and precisely.

Nevertheless, the eye searching area established by the conventional eye detection apparatus is a rectangle area with a horizontal side and a vertical side greater than the horizontal side, which covers a large area including eyebrows and cheeks. This obviously results another problems that the conventional eye detection apparatus would take much more time on finding out the upper/lower eyelids on the large eye searching area.

SUMMARY OF INVENTION

The present invention is directed to a method and an apparatus, which can solve the aforementioned programs that the conventional eye detection apparatus would take much more time on finding out a certain part of the eye, such as the upper/lower eyelids on the large eye searching area.

Specifically, the present invention relates to an eye state detection apparatus, which comprises a storage unit, a camera unit and a processing unit. The camera unit is configured for capturing an original image of a user's face. The storage unit is configured for storing a program and the original image of the user's face. The processing unit is electrically connected with the camera unit and the storage unit, and is configured to load and execute the program to perform eye detection. Specifically, when the processing unit loads and executes the program, the program causes the processing unit to receive an original image, obtain a face image from the original image; define each center point of two nostrils respectively on the face image, compute a distance D between the two center points of the two nostrils and determining coordinates of an initial point A (x1, y1), determine coordinates of a reference point B (x2, y2) according to the distance D and the initial point A (x1, y1), define a rectangle on the face image according to the coordinates of the reference point B (x2, y2), and obtain an eye image of the user's eye from an area of the rectangle. The above-mentioned the initial point A (x1, y1) represents a midpoint between the two center points of the two nostrils, and x2=x1+k1×D, y2=y1+k2×D, k1=1.6~1.8, k2=1.6~1.8, preferably k1=k2. The reference point B (x2, y2) represents a middle point of the rectangle. The rectangle has a width in a vertical direction and a length in a horizontal direction that is greater than the width; and the eye image include the user's eye thereon.

Preferably, the program further cause the processing unit to be programmed to perform an eye state estimation based on the eye image to obtain an upper eyelid feature on the eye image, determine a curved level of the upper eyelid feature and generate an eye state data based on the determined result, wherein the eye state data represents either opening eye state or closing eye state.

The present invention is further directed to an eye searching apparatus, comprising a processing unit and a program, wherein the processing unit is configured to execute the program to perform eye detection. Specifically, when the processing unit executes the program, the program causes the processing unit to be programmed to run the following steps of the eye searching method and state estimation step. The eye state estimation step is to obtain the upper eyelid feature on the eye image, determine a curvature level of the upper eyelid feature, and generate an eye state data representing either opening eye state or closing eye state. The steps includes: a) defining each center point of two nostrils respectively on a face image; b) computing a distance D between the two center points of the two nostrils and a midpoint between the two center points of the two nostrils; and c) obtaining an eye from the face image based on the distance D and the midpoint. Preferably, the aforementioned step c) further includes: determining a reference point having coordinates (k1×D, k2×D), and defining a rectangle around the reference point as its center, wherein k1=1.6~1.8, k2=1.6~1.8, the rectangle has a width in a vertical direction and a length in a horizontal direction greater than the width, and the rectangle surrounds the eye of the face image. The k1 mentioned above is preferably equal to k2.

Compared with the prior art, it is believed that the eye image or the above-mentioned rectangle obtained by the present invention includes the eye thereon, which has smaller area than the eye searching area in the prior art. As such, it is easier for the processing unit of the present invention to quickly obtain a certain part of the eye by searching the smaller area on the image.

Other features, objects, aspects and advantages will be identified and described in detail below.

DETAILED DESCRIPTION OF EMBODIMENTS

Figure 1:
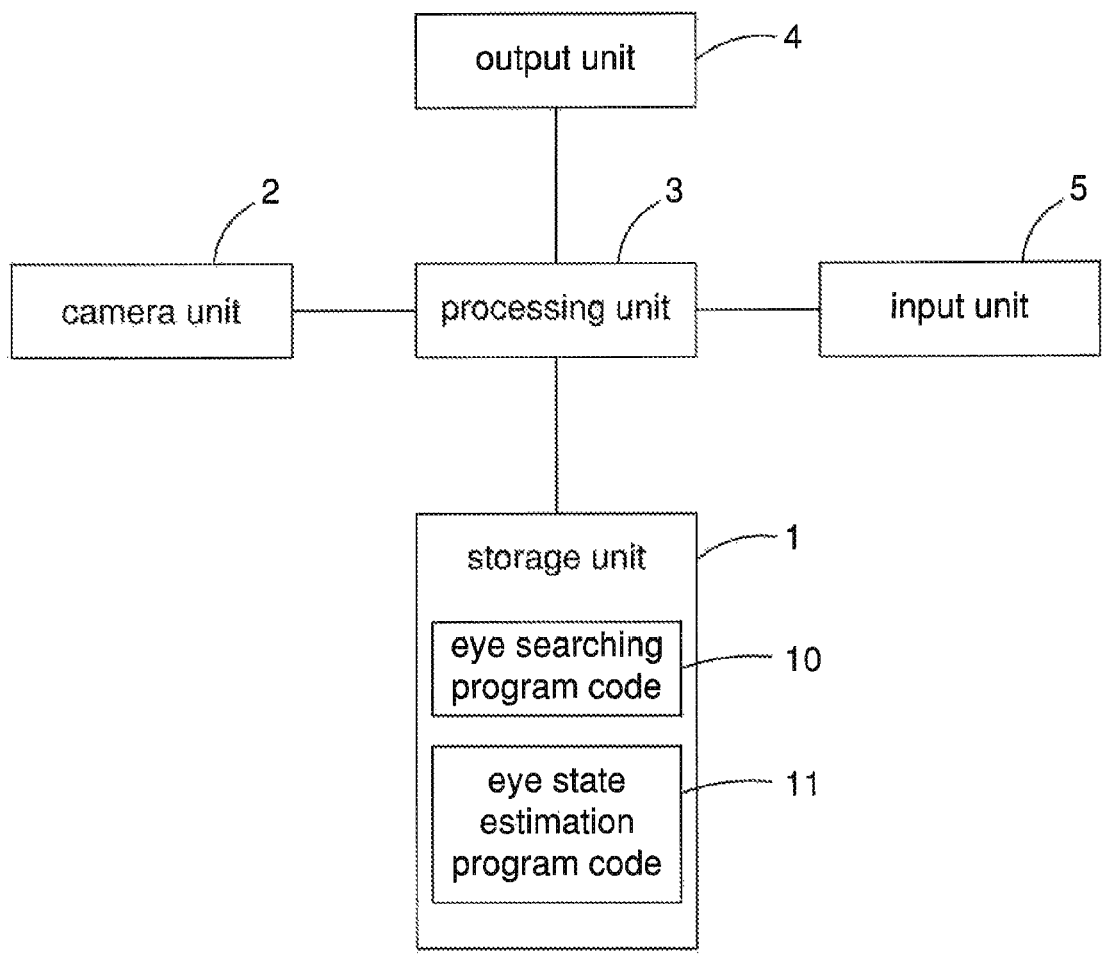
FIG. 1 is a block diagram of an eye state detection apparatus in accordance with an embodiment of the present invention.

With reference to FIG. 1, a block diagram of an eye state detection apparatus is shown in accordance with an embodiment of the present invention. The eye state detection apparatus comprises a storage unit 1, a camera unit 2, a processing unit 3, an output unit 4 electrically connected to the processing unit 3, and an input unit 5 (that consists of several buttons). The storage unit 1 consists of one or several non-volatile access memory, which stores a program and the original image of the user's face captured by the camera unit 1. The program has a set of eye detection program code 10, preferably further includes a set of eye state estimation program code 11. The camera unit 1 is configured to capture a user's face to produce several successive original images and send the images to the storage unit 1 for temporally storing thereon.

The camera unit 2 is preferably a rotatable lens (not shown in the drawings) that can be rotated at any angle and in any direction, allowing the lens to face the user's, face at a certain elevation angle, such as an elevation angle of 45 degree. As such, the nostrils on each of the face images captured by the camera unit 2 can be clearly shown. This means that the legibility of the nostrils on each of the face images can be significantly increased, which benefits the follow-up nostril searching process. In general, the camera unit 2 further includes an illumination device for emission of light to ensure great quality of the face image.

Figure 2:
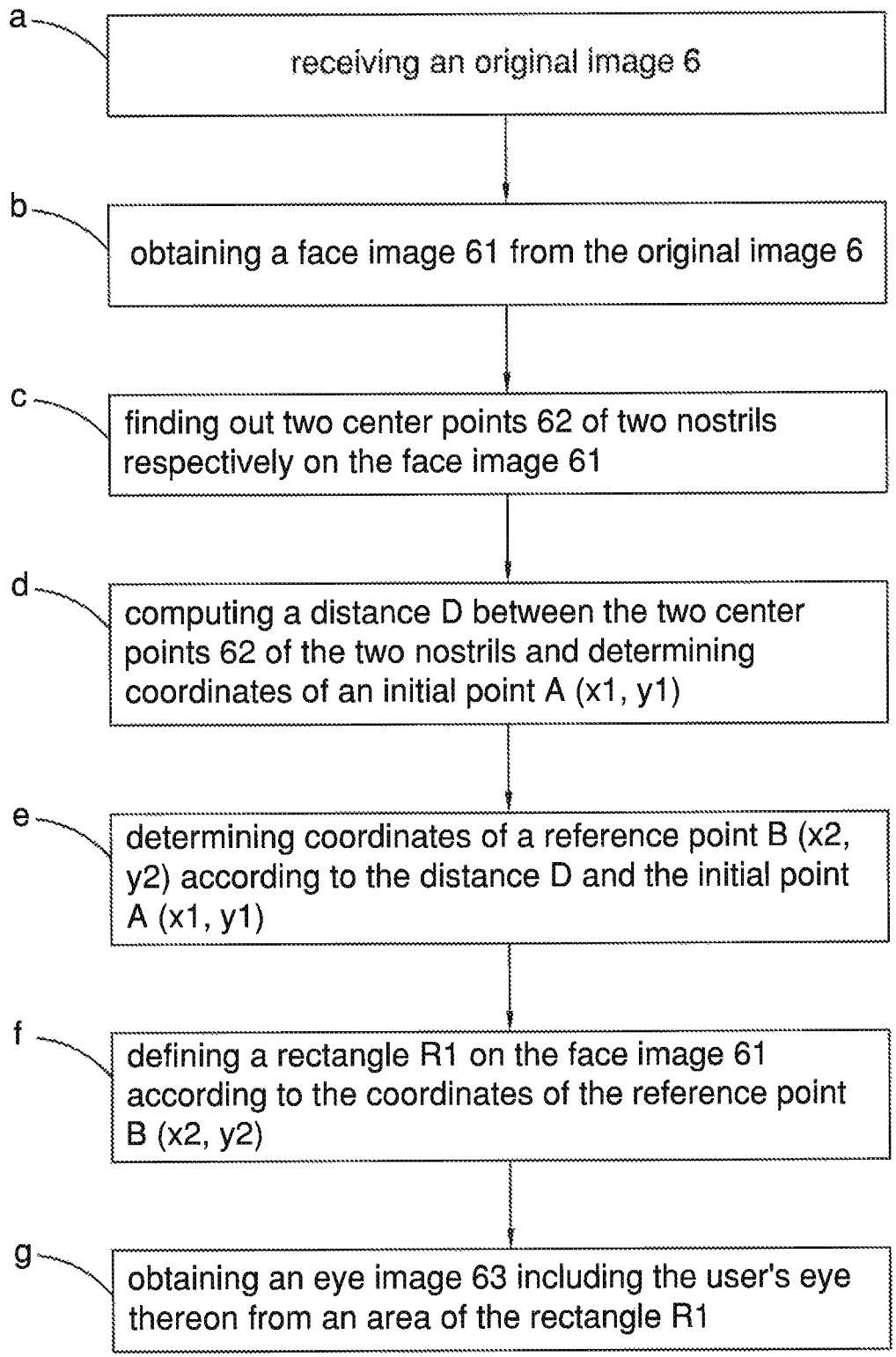
FIG. 2 is a process flow diagram that illustrates instructions executed by the processing unit object in accordance with an embodiment of the present invention.
Figure 3:
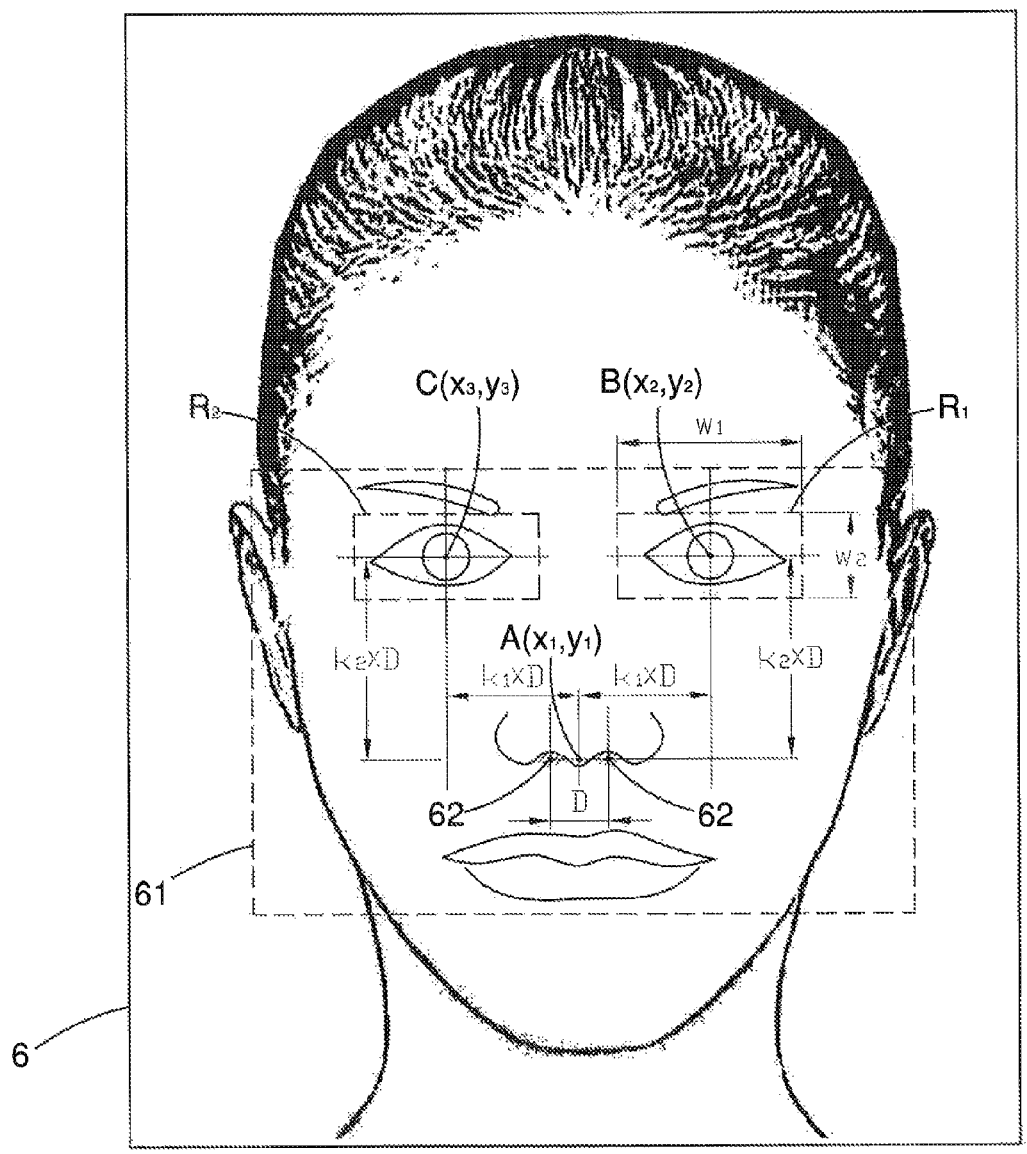
FIG. 3 is a perspective view of an image captured by the camera unit in accordance with an embodiment of the present invention.
Figure 4:
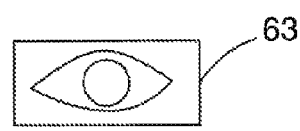
FIG. 4 is a perspective view of an eye image obtained form the image in accordance with an embodiment of the present invention.

The processing unit 3 is electrically connected to the camera unit 2 and the storage unit 1, which includes at least a central processing unit (CPU, not shown) and a random-access memory (RAM, not shown). When the processing unit 3 loads and executes the eye searching program code 10, the processing unit 3 is programmed to run the following tasks, as shown in FIGS. 2 and 3, including:

a) receiving an original image 6 (block a of FIG. 2), wherein the original image 6 is obtained by capturing the user's face through the camera unit 2; and the original image 6 includes not only the user's face, but also some unnecessary parts that are needed to be removed, such as hair, neck and background;

b) obtaining a face image 61 from the original image 6 (block b of FIG. 2), which can be performed by Adaboost algorithm and other image processing techniques, Wherein the unnecessary portions mentioned above have partially or completely been removed from the illustrative face image 61 preferably;

c) defining each center point 62 of two nostrils respectively on the face image 61 (block c of FIG. 2), wherein the way to define the two center points of the two nostrils on the face image has been disclosed in the prior art, which would not be illustrated hereinafter; the center points 62 of the two nostrils can be respectively defined by creating an intersection of the longest transverse and longest longitudinal axes of each nostril area as the nostril area on the face image 61 is obviously darker than the other areas;

d) computing a distance D between the two center points 62 of the two nostrils and determining coordinates of an initial point A (x1, y1) (block d of FIG. 2), wherein the coordinates of the initial point A (x1, y1) represents a midpoint between the two center points of the two nostrils;

e) determining coordinates of a reference point B (x2, y2) according to the distance D and the initial point A (x1, y1) (block e of FIG. 2), wherein $x2=x1+k1 \times D$, $y2=y1+k2 \times D$, $k1=1.6 \sim 1.8$, $k2=1.6 \sim 1.8$, and preferably, $k1=k2$; it is noted that the reference point B (x2, y2) locates at or near to a midst point of an eye of the face image 61 according to the real experiential results; wherein similarly, coordinates of another reference point C (x3, y3) can be further determined according to the distance D and the initial point A (x1, y1) if necessary, wherein $x3=x1-k1 \times D$, $y3=y1-k2 \times D$; and it is noted that the illustrative reference point C (x3, y3) locates at or near to a midst point of another eye of the face image 61;

f) defining a rectangle R1 on the face image 61 according to the coordinates of the reference point B (x2, y2) (block f of FIG. 2); wherein the coordinates of the reference point B (x2, y2) represents a middle point of the rectangle R1; the rectangle R1 has a length W1 in a horizontal direction and a width W2 in a vertical direction, $W1=30 \sim 50$ pixel, $W2=15 \sim 29$ pixel, $W1>W2$, preferably $W1=40$ pixel, $W2=25$ pixel; and wherein similarly, another rectangle R2 that is the same as the rectangle R1 can be further defined according to the coordinates of the reference point C (x3, y3) if necessary, wherein the coordinates of the reference point C (x3, y3) represents a middle point of the rectangle R2; and g) obtaining an eye image 63 including the user's eye thereon from an area of the rectangle R1 (block g of FIG. 2), as shown in FIG. 4; wherein it is noted that another eye image from an area of the rectangle R2 can be further obtained if necessary.

It is understood that the rectangle R1 from bock f surrounds one eye of the face image 61 according to the real results. Moreover, it is believed that either the eyebrows above the eye or the cheeks below the eye does not locate within the illustrative rectangle R1 (alternatively may a few part of the eyebrows locate within the rectangle R1). Also, similarity, the other rectangle R2 surrounds the other eye of the face image 61, which may exclude the eyebrows and the cheeks thereon. This means that the eye image 61 from block g includes the eye thereon, and an area of any one of the eye images of the present invention is much smaller than the eye searching area in prior art.

The processing unit 3 would further continue loading and executing the eye state estimation program code 11 after obtaining the eye image 63 or the two eye images 63. The eye state estimation program code 11 causes the processing unit 3 to be programmed to run an eye state estimation step to define a certain part of the eye on the eye image 63, such as upper/lower eyelid feature or pupil feature, and generate an eye state data according to detected result of the certain part of the eye. The illustrative eye state data includes either "0" representing opening eye state or "1" representing closing eye state, for example. In the present invention, the eye state data is obtained by determining a curvature level of the upper eyelid. Specifically, when the eye is opening, the upper eyelid shows a cured line relative to the horizontal direction; on the contrary, when the eye is closing, the upper eyelid shows an approximate straight line relative to the horizontal direction. After processing the eye image 63 by an image processing technology, an upper eyelid image can be created from the upper eyelid of the eye image 63. If the eye on the eye image 63 is opening, the upper eyelid image shows a parabolic curved line, which indicates that a focal length of the parabolic curved line can be calculated by the processing unit 3 according to the parabolic equation. However, if the eye on the eye image 63 is closing, the upper eyelid image shows a straight line, which obviously means that the focal length thereof extends into infinity. In a word, the processing unit 3 processes the eye image 63 to generate a focal length, the different focal lengths represent different curvature level of the upper eyelid, and different curvature levels of the upper eyelid indicate different eye state. More specifically, when the focal lengths obtained from the processing unit 3 by processing successive images gradually increase from a certain value to infinity, the eye on the captured image is then determined as the closing eye state and therefore the eye state data "1" representing closing eye state is generated. On the contrary, when the focal lengths obtained by processing successive images gradually decrease from infinity to a certain value, the eye on the captured image is then determined as the opening eye state and therefore the eye state data "0" representing opening eye state is generated.

Information needed for carrying out the aforementioned tasks by the processing unit 3 or generated from the processing unit 3, such as the face image or the eye image, is stored in the storage unit 1. The information may be temporally stored or permanently saved in the storage unit 1 depending on the needs.

As illustrated above, it is understood that the eye state detection apparatus can take an image of the user's face by the camera unit 2, process each of the images by the processing unit 3, and generate an eye state data depending upon the results from processing unit 3 by processing each of the images. For example, if the eye state data shows "1" representing closing eye state, or the eye state data "1" shows very often with increasing frequency higher than a threshold, the processing unit 3 determines that the user is dozing off. At this time, the output unit 4 is driven to transmit an alarm message, such as an alarm sound output from a loudspeaker of the output unit 4. Preferably, the output unit 4 further includes a display device (such as a touched panel) for displaying the alarm message or other related information thereon (such as an the human-computer interface for setting operations).

According to the above descriptions from task a to task b, the processing unit 4 actually is to perform an eye searching method, including steps of:

defining each center point of two nostrils on a face image respectively;

computing a distance D between the two center points of the two nostrils and a midpoint between the two center points of the two nostrils;

determining a reference point having the coordinates (k1×D, k2×D), wherein k1=1.6~1.8, k2=1.6~4.8, preferably k1=k2; and defining a rectangle around the reference point as its center, wherein the rectangle has a length W1 in a horizontal direction and a width W2 in a vertical direction, W1=30~50 pixel, W2=15~29 pixel and W1>W2, preferably W1=40 pixel and W2=25 pixel.

Compared with the prior art, it is believed that the eye image or the above-mentioned rectangle obtained by the present invention includes the eye thereon, which has smaller area than the eye searching area in the prior art. As such, it is easier for the processing unit 3 of the present invention to quickly find out a certain part of the eye by searching the smaller area on the image.

It will be appreciated that although a particular embodiment of the invention has been shown and described, modifications may be made. It is intended in the claims to cover such modifications which come within the spirit and scope of the invention.

The invention claimed is:

1. An eye state detection apparatus, comprising:
a camera unit configured for capturing an original image of a user's face;
a storage unit configured for storing a program and the original image of the user's face; and
a processing unit electrically connected with the camera unit and the storage unit, the processing unit configured to load and execute the program to receive the original image, obtain a face image from the original image, define each center point of two nostrils on the face image, compute a distance D between the two center points of the two nostrils and determine coordinates of an initial point A (x1, y1) representing a midpoint between the two center points of the two nostrils, determine coordinates of a reference point B (x2, y2) according to the distance D and the initial point A (x1, y1), define a rectangle on the face image according to the coordinates of the reference point B (x2, y2), and obtain an eye image of the user's eye from an area of the rectangle;
wherein x2=x1+k1×D, y2=y1+k2×D, k1=1.6~1.8, k2=1.6~1.8, and the coordinates of the reference point B (x2, y2) represents a middle point of the rectangle.

2. The apparatus of claim 1, wherein k1=k2.

3. The apparatus of claim 1, wherein the processing unit is further to perform an eye state estimation based on the eye image to obtain an upper eyelid feature on the eye image, determine a curved level of the upper eyelid feature and generate an eye state data based on the determined result, wherein the eye state data represents either opening eye state or closing eye state.

4. The apparatus of claim 3, wherein the eye state estimation is performed by the process unit, in which the upper eyelid feature on the eye image is presented as a parabolic curved line with a focal length, the curved level of the upper eyelid feature is determined by the focal length, and if focal lengths obtained by processing successive eye images gradually increase from a certain value, the eye is then determined as in the closing eye state, and if the focal lengths gradually decrease to a certain value, the eye is then determined as in the opening eye state.

5. The apparatus of claim 4, wherein if the eye state data shows that the eye is in the closing eye state with an occurring frequency higher than a threshold, the processing unit determines that the user is dozing off.

6. An eye searching method, comprising the following steps of:
a) defining each center point of two nostrils on a face image respectively;
b) computing a distance D between the two center points of the two nostrils and a midpoint between the two center points of the two nostrils; and
c) obtaining an eye on the face image based on the distance D and the midpoint;
wherein step c further comprises:
determining a reference point having the coordinates (k1×D, k2×D), wherein k1=1.6~1.8, k2=1.6~1.8; and
defining a rectangle around the reference point as its center, wherein the rectangle has a width in a vertical direction and a length in a horizontal direction greater than the width, and the rectangle surrounds the eye of the face image.

7. The method of claim 6, wherein k1=k2.

8. An eye searching apparatus comprising a processing unit and a program, wherein the processing unit is configured to execute the program to define each center point of two nostrils respectively from a face image, compute a distance D between the two center points of the two nostrils and a midpoint between the two center points of the two nostrils, and obtain an eye from the face image based on the distance D and the midpoint; and wherein the processing unit is further configured to determine a reference point has the coordinates (k1×D, k2×D), and define a rectangle around the reference point as its center, wherein k1=1.6~1.8, k2=1.6~1.8, the rectangle has a width in a vertical direction and a length in a horizontal direction greater than the width, and the rectangle surrounds the eye of the face image.

9. The apparatus of claim 8, wherein k1=k2.

* * * * *